(12) United States Patent
Kramer et al.

(10) Patent No.: US 9,279,027 B1
(45) Date of Patent: *Mar. 8, 2016

(54) PHOTOACID GENERATOR COMPOUND, POLYMER COMPRISING END GROUPS CONTAINING THE PHOTOACID GENERATOR COMPOUND, AND METHOD OF MAKING

(71) Applicant: Dow Global Technologies LLC, Midland, MI (US)

(72) Inventors: John W. Kramer, Midland, MI (US); Daniel J. Arriola, Midland, MI (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 230 days.

This patent is subject to a terminal disclaimer.

(21) Appl. No.: 14/012,065

(22) Filed: Aug. 28, 2013

Related U.S. Application Data

(60) Provisional application No. 61/695,733, filed on Aug. 31, 2012.

(51) Int. Cl.
| | | |
|---|---|---|
| C07C 327/32 | (2006.01) | |
| C08F 222/10 | (2006.01) | |
| G03F 7/004 | (2006.01) | |
| G03F 7/039 | (2006.01) | |
| C07C 327/34 | (2006.01) | |
| C07F 7/08 | (2006.01) | |
| C07D 333/76 | (2006.01) | |

(52) U.S. Cl.
CPC ............. C08F 222/10 (2013.01); C07C 327/34 (2013.01); C07D 333/76 (2013.01); C07F 7/0809 (2013.01); G03F 7/0045 (2013.01); G03F 7/039 (2013.01)

(58) Field of Classification Search
CPC ............................ C07C 327/36; C07C 333/76
See application file for complete search history.

(56) References Cited

U.S. PATENT DOCUMENTS

| 6,140,010 | A | 10/2000 | Iwasa et al. | |
|---|---|---|---|---|
| 6,888,020 | B2 | 5/2005 | Kim et al. | |
| 7,666,962 | B2 | 2/2010 | Le et al. | |
| 7,696,292 | B2 | 4/2010 | Farnham et al. | |
| 7,834,113 | B2 | 11/2010 | Sounik et al. | |
| 9,052,589 | B2 * | 6/2015 | Kramer | G03F 7/0041 |
| 2003/0195310 | A1 * | 10/2003 | McCormick | C07C 327/36 526/193 |
| 2004/0242798 | A1 | 12/2004 | Sounik et al. | |
| 2005/0032997 | A1 | 2/2005 | Lee et al. | |
| 2006/0257781 | A1 | 11/2006 | Benoit et al. | |
| 2008/0008965 | A1 | 1/2008 | Ohashi et al. | |
| 2008/0102407 | A1 | 5/2008 | Ohsawa et al. | |
| 2009/0035699 | A1 | 2/2009 | Hasegawa et al. | |
| 2009/0081588 | A1 | 3/2009 | Hatakeyama et al. | |
| 2009/0269696 | A1 | 10/2009 | Ohsawa et al. | |
| 2010/0048844 | A1 | 2/2010 | Shih et al. | |
| 2010/0055608 | A1 | 3/2010 | Ohashi et al. | |
| 2010/0099042 | A1 | 4/2010 | Ohashi et al. | |
| 2011/0200941 | A1 | 8/2011 | Masunaga et al. | |
| 2012/0077127 | A1 | 3/2012 | Sills et al. | |
| 2012/0129103 | A1 | 5/2012 | Ohsawa et al. | |
| 2012/0202141 | A1 | 8/2012 | Inasaki et al. | |
| 2014/0065550 | A1 | 3/2014 | Kramer et al. | |

FOREIGN PATENT DOCUMENTS

| CN | 102070742 | A | 5/2011 |
|---|---|---|---|
| JP | 2014094932 | A | 5/2014 |
| WO | 9801478 | A1 | 1/1998 |
| WO | 03066685 | A2 | 8/2003 |
| WO | 2004056880 | A1 | 7/2004 |
| WO | 2008142209 | A1 | 11/2008 |

OTHER PUBLICATIONS

Gallatin et al.; "Fundamental Limits to EUV Photoresist"; Advances in Resist Materials and Processing Technology XXIV, edited by Qinghuang Lin; Proc. of SPIE; vol. 6519; 651911-1; (2007), 10 pages.

Kim et al.; "Synthesis of Photoacid Generator-Containing Patternable Diblock Copolymers by Reversible Addition—Fragmentation Transfer Polymerization"; Chem. Mater.; 21; pp. 3030-3032; (2009), 3 pages.

Moad et al., "Advances in RAFT polymerization: the synthesis of polymers with defined end-groups" Polymer 46 (2005) 8458-8468; 11 pages.

(Continued)

Primary Examiner — Rosalynd Keys
(74) Attorney, Agent, or Firm — Cantor Colburn LLP

(57) ABSTRACT

A compound has formula (I):

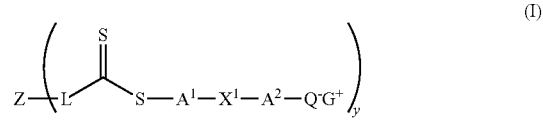

wherein in formula (I), Z is a y valent $C_{1-20}$ organic group, $A^1$ and $A^2$ are each independently ester containing or non-ester containing and are fluorinated or non-fluorinated, and are independently $C_{1-40}$ alkylene, $C_{3-40}$ cycloalkylene, $C_{6-40}$ arylene, or $C_{7-40}$ aralkylene, and $A^1$ contains a nitrile, ester, or aryl substituent group alpha to the point of attachment with sulfur, L is a heteroatom or a single bond, $X^1$ is a single bond, —O—, —S—, —C(=O)—O—, —O—C(=O)—, —O—C(=O)—O—, —C(=O)—NR—, —NR—C(=O)—, —NR—C(=O)—NR—, —S(=O)$_2$—O—, —O—S(=O)$_2$—O—, —NR—S(=O)$_2$—, or —S(=O)$_2$—NR, wherein R is H, $C_{1-10}$ alkyl, $C_{3-10}$ cycloalkyl or $C_{6-10}$ aryl, $Q^-$ is an anionic group, $G^+$ is a metallic or non-metallic cation, and y is an integer from 1 to 6. A polymer having end groups comprising the reaction product of the compound of formula (I), and a method of making a polymer, are also disclosed.

10 Claims, No Drawings

(56) References Cited

OTHER PUBLICATIONS

Sheehan et al., "RAFT Technology for the Production of Advanced Photoresist Polymers" Advances in Resist Materials and Processing Technology XXV, Proc. of SPIE vol. 6923, 69232E-69232E-9, (2008), 4 pages.

CN 101078879 A with English Abstract; Date of Publication: Nov. 11, 2007; 58 pages.

Non-Final Office Action dated Dec. 1, 2014; U.S. Appl. No. 14/012,174, filed Aug. 28, 2013.

* cited by examiner

PHOTOACID GENERATOR COMPOUND, POLYMER COMPRISING END GROUPS CONTAINING THE PHOTOACID GENERATOR COMPOUND, AND METHOD OF MAKING

BACKGROUND

Design rules for advanced generation microlithography (i.e., such as e-beam, X-ray, and extreme ultraviolet (EUV) lithography operating at a wavelength of 13.4 nm) are trending toward ever smaller dimensions of, for example, 30 nm and below. The narrower linewidths and thinner resist films used in advanced generation lithography can give rise to consistency issues such as line width roughness (LWR), where resolution takes on increasing significance and limits the performance and usefulness of photoresists. Excessive LWR can lead to poor etch and lack of linewidth control in, for example, transistor and gate architecture, potentially causing short circuits and signal delay in the final devices.

Uneven distribution of photoacid generators (PAGs) for catalyzing deprotection of protected developable groups in photoresist films may contribute to increased LWR and hence poor resolution. PAGs may be incorporated into photoresist formulations by preparing a physical blend of the PAG and a photoresist polymer where, upon spin coating, an inhomogeneous distribution of PAG may occur in the photoresist film, leading to uneven acid generation and greater line edge roughness (LER). Alternatively, the PAG can be attached to the polymer backbone, limiting its mobility in the formulation. While this strategy can improve PAG dispersion in a photoresist film and hence improve pattern formation, the PAGs nonetheless are doubly distributed between both the polymer chains (where some chains may contain more PAG than others) and within a polymer chain (where some chain regions may contain more PAG than others depending on the reactivity ratio of a PAG-containing monomer). More uniform PAG dispersion methods are therefore desirable.

Control of composition, molecular weight, and polydispersity are thus useful for improving PAG dispersion in a photoresist film. Acrylate-based EUV photoresist polymers may be synthesized by modified free radical polymerization techniques in which control of monomer and initiator feed rates help control the composition, but termination and chain transfer reactions can lead to different compositions occurring at different points during a polymerization, and a relatively broad distribution of molecular weights. Because variation in composition affects photoresist solubility, a broad composition distribution across chains and broad molecular weight distributions are not desirable.

Controlled radical polymerization methods can be used to prepare (meth)acrylate containing polymers with polydispersities of less than 2.0. One method of controlled radical polymerization involves use of dithioester chain transfer agents (CTA) to control molecular weight distributions. As described in *Proc. of SPIE Vol.* 6923, 2008, 69232E-1-69232E-9, reversible addition fragmentation transfer (RAFT) polymerization techniques have been used to produce photoresist polymers for 193 nm lithography. Accurate and specific molecular weights may be obtained based on the amount of CTA, and because the CTAs are chain terminators, it is possible to end-group functionalize polymers made using CTAs.

STATEMENT OF INVENTION

One or more of the above and other deficiencies of the prior art may be overcome by a compound in accordance with the invention, having formula (I):

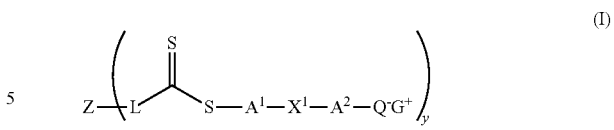

wherein in formula (I), Z is a y valent $C_{1-20}$ organic group, $A^1$ and $A^2$ are each independently ester containing or non-ester containing and are fluorinated or non-fluorinated, and are independently $C_{1-40}$ alkylene, $C_{3-40}$ cycloalkylene, $C_{6-40}$ arylene, or $C_{7-40}$ aralkylene, and $A^1$ contains a nitrile, ester, or aryl substituent group alpha to the point of attachment with sulfur, L is a heteroatom or a single bond, $X^1$ is a single bond, —O—, —S—, —C(=O)—O—, —O—C(=O)—, —O—C(=O)—O—, —C(=O)—NR—, —NR—C(=O)—, —NR—C(=O)—NR—, —S(=O)$_2$—O—, —O—S(=O)$_2$—O—, —NR—S(=O)$_2$—, or —S(=O)$_2$—NR—, wherein R is H, $C_{1-10}$ alkyl, $C_{3-10}$ cycloalkyl or $C_{6-10}$ aryl, Q$^-$ is an anionic group, G$^+$ is a metallic or non-metallic cation, and y is an integer of 1 to 6.

A polymer comprises end groups derived from the reaction product of the compound of formula (1), an unsaturated monomer, and optionally, an initiator.

A method of making a polymer comprises polymerizing one or more unsaturated monomers in the presence of a compound having formula (I):

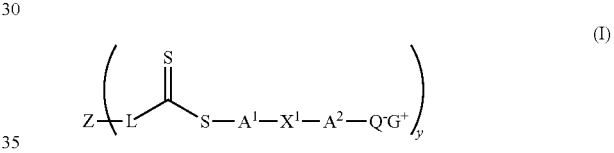

wherein in formula (I), Z is a y valent $C_{1-20}$ organic group, $A^1$ and $A^2$ are each independently ester containing or non-ester containing and are fluorinated or non-fluorinated, and are independently $C_{1-40}$ alkylene, $C_{3-40}$ cycloalkylene, $C_{6-40}$ arylene, or $C_{7-40}$ aralkylene, and $A^1$ contains a nitrile, ester, or aryl substituent group alpha to the point of attachment with sulfur, L is a heteroatom or a single bond, $X^1$ is a single bond, —O—, —S—, —C(=O)—O—, —O—C(=O)—, —O—C(=O)—O—, —C(=O)—NR—, —NR—C(=O)—, —NR—C(=O)—NR—, —S(=O)$_2$—O—, —O—S(=O)$_2$—O—, —NR—S(=O)$_2$—, or —S(=O)$_2$—NR—, wherein R is H, $C_{1-10}$ alkyl, $C_{3-10}$ cycloalkyl or $C_{6-10}$ aryl, Q$^-$ is an anionic group, G$^+$ is a metallic or non-metallic cation, and y is an integer of 1 to 6; and optionally, an initiator.

DETAILED DESCRIPTION

Disclosed herein are novel compounds for use as chain transfer agents (CTAs) for reversible addition fragmentation transfer (RAFT) controlled polymerization reactions. The CTAs contain, in addition to a sulfur-containing moiety (e.g. dithionate or similar moiety) which upon fragmentation reacts with an available radical, an anionic moiety and corresponding cation. Preferably, the cation is an onium cation, such as an iodonium or a sulfonium cation, capable of photolytically generating an acidic proton when exposed to actinic radiation. Also preferably, the sulfur containing moiety of the compound is attached by a linking group to the anionic moiety. The CTA compounds disclosed herein are useful for preparing narrow polydispersity (PDI<2.0) polymers with photoacid generating end groups. Such polymers can in turn be used to prepare photoresists having well dispersed photoacid generator moieties within a photoresist matrix.

As used herein, "polymer" includes a polymer having two or more different monomeric units, and includes copolymers having two monomeric units, terpolymers having three monomeric units, tetrapolymers having four monomeric units, pentapolymers having five monomeric units, etc. It will also be appreciated that the copolymers disclosed herein may be random copolymers, block copolymers, gradient copolymers, alternating copolymers, or a combination including two or more of these motifs. The polymer may also have a compositional gradient. Preferably, the copolymers are random copolymers, where no particular order of the monomers is implied by the formulas.

As used herein, an "aryl" is an aromatic group and may be monocyclic, for example, a phenyl group; polycyclic, for example, a biphenyl group; or fused polycyclic, for example, a naphthyl group, and it will be understood that "aryl" includes all aromatic structures including those of fewer than 6 carbon atoms such as heteroaromatic compounds including pyrazoles, thiophenes, oxazoles, pyridines, etc. Also as used herein, an "alkyl" group is an $sp^3$ hybridized carbon containing group and may be linear or branched, and may include cycloalkyl unless otherwise specified. As used herein, "aralkyl" means a group which contains both an aryl moiety and an alkyl moiety, where either the aryl or the alkyl group is the point of attachment to the adjacent radical. Similarly, "arylene", "alkylene", "cycloalkylene", and "aralkylene" groups are divalent aryl, alkyl, and aralkyl groups respectively. It should be noted that an aralkylene group has points of attachment at both the aryl and alkyl portions. Furthermore, one or more structural (as opposed to substituent) atoms of an aryl, arylene, cycloalkyl, cycloalkylene, aralkyl, or aralkylene, may be replaced with one or more heteroatoms. Preferred heteroatoms include oxygen, nitrogen, phosphorus, sulfur, and silicon.

Further, "anion-bound" means that an organic linking group, e.g., an alkyl, aryl, alkoxy, polyalkoxy, ester, carbonate, amide, urea, sulfonate, sulfate, sulfonimide, sulfonamide, acetal or ketal-containing group, or other appropriate group, forms a covalently bonded structure between the anion of the PAG and the sulfur-containing end group of the RAFT moiety. Also as used herein, "substituted" means including a substituent such as a halogen (i.e., F, Cl, Br, I), hydroxy, amino, thiol, carboxyl, carboxylate, amide, nitrile, thiol, sulfide, disulfide, nitro, a $C_{1-10}$ alkyl, a $C_{1-10}$ alkoxy, a $C_{6-10}$ aryl, a $C_{6-10}$ aryloxy, a $C_{7-10}$ alkyl aryl, a $C_{7-10}$ alkyl aryloxy, or a combination comprising at least one of the foregoing. It will be understood that any group or structure disclosed with respect to the formulas herein may be so substituted unless otherwise specified, or where such substitution would significantly adversely affect the desired properties of the resulting structure.

Thus, a RAFT agent includes a compound having formula (I):

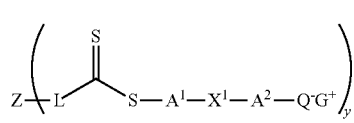

(I)

wherein, in formula (I), Z is a y valent $C_{1-20}$ organic group. Preferably, Z is a $C_{1-20}$ alkyl, $C_{3-20}$ cycloalkyl, $C_{6-20}$ aryl, or $C_{7-20}$ aralkyl group. Exemplary such groups include methyl, ethyl, hexyl, octyl, dodecyl, undecyl, cyclohexyl, neopentyl, phenyl, benzyl, cyclohexylene, phenylene, naphthylene, and xylylene. Preferably, y is an integer of 1 to 6, and preferably, 1 to 4. It will be understood that the value of y does not exceed the available valences for group Z.

Also in formula (I), $A^1$ and $A^2$ are each independently ester containing or non-ester containing, fluorinated or non-fluorinated groups, and are independently $C_{1-40}$ alkylene, $C_{3-40}$ cycloalkylene, $C_{6-40}$ arylene, or $C_{7-40}$ aralkylene. It will be appreciated that $A^1$ contains a radical stabilizing group including a nitrile, ester, or aryl substituent group alpha to the point of attachment with sulfur, to afford resonance stability of a radical generated adjacent to this point in the molecule. Preferably, $A^1$ is a $C_{1-20}$ alkylene, $C_{3-20}$ cycloalkylene, $C_{6-20}$ arylene, or $C_{7-20}$ aralkylene substituted alpha to the point of attachment with sulfur with a CN, $C_{6-10}$ aryl, or an ester of a $C_{1-10}$ alcohol. Also preferably, $A^2$ is fluorinated or non-fluorinated, and is $C_{1-20}$ alkylene, $C_{3-20}$ cycloalkylene, $C_{6-20}$ arylene, or $C_{7-20}$ aralkylene.

As used throughout this specification, "fluoro" or "fluorinated" means that one or more fluorine groups are attached to the associated group. For example, by this definition and unless otherwise specified, "fluoroalkyl" encompasses monofluoroalkyl, difluoroalkyl, etc., as well as perfluoroalkyl in which substantially all carbon atoms of the alkyl group are substituted with fluorine atoms; similarly, "fluoroaryl" means monofluoroaryl, perfluoroaryl, etc. "Substantially all" in this context means greater than or equal to 90%, preferably greater than or equal to 95%, and still more specifically greater than or equal to 98% of all atoms attached to carbon are fluorine atoms.

Also in formula (I), L is a heteroatom or a single bond. Heteroatom, as used in this circumstance and unless otherwise specified, includes a divalent or polyvalent heteroatom such as O, N, P, S, Si, where for heteroatoms such as, for example, N, P, and Si, the unfilled valences are substituted with R (e.g., NR, PR, $PR_3$, $SR_2$, $SiR_2$, etc.), where R is H, $C_{1-10}$ alkyl, $C_{3-10}$ cycloalkyl, $C_{6-10}$ aryl, or $C_{7-10}$ aralkyl. Preferably, $X^1$ is a —C(=O)—O— or —O—C(=O)—.

Linking group $X^1$ in formula (I) includes a single bond, —O—, —S—, —C(=O)—O—, —O—C(=O)—, —O—C(=O)—O—, —C(=O)—NR—, —NR—C(=O)—, —NR—C(=O)—NR—, —S(=O)$_2$—O—, —O—S(=O)$_2$—O—, —NR—S(=O)$_2$—, or —S(=O)$_2$—NR, wherein R is H, $C_{1-10}$ alkyl, $C_{3-10}$ cycloalkyl or $C_{6-10}$ aryl. Preferably, $X^1$ is a single bond, —O—, —C(=O)—O—, —O—C(=O)—, —O—C(=O)—O—, or —S(=O)$_2$—O—.

$Q^-$ in formula (I) is an anionic group and includes sulfonate, sulfate, sulfonamide anion, or sulfonimide anion group. Preferably, Q is an anionic group including a sulfonate (—SO$_3^-$), the anion of a sulfonamide (—SO$_2$(N$^-$)R' where R' is a $C_{1-10}$ alkyl or $C_{6-20}$ aryl, or the anion of a sulfonimide. Where $Q^-$ is a sulfonimide anion, the sulfonimide may be an asymmetric sulfonimide having the general structure —SO$_2$—(N$^-$)—SO$_2$—R", where R" is a straight chain or branched $C_{1-10}$ fluoroalkyl group. Preferably, the R" group is a $C_{1-4}$ perfluoroalkyl group, and is derived from the corresponding perfluorinated alkanesulfonic acid, such as trifluoromethanesulfonic acid or perfluorobutanesulfonic acid.

Formula (I) further comprises a cation G$^+$. G$^+$ is a metallic or non-metallic cation. Preferably, G is an alkali metal cation, ammonium cation, alkylammonium cation, alkyl-aromatic ammonium cation, sulfonium cation, iodonium cation, phosphonium cation, or a carbonium cation which may be a metal or non-metal cation. Preferred non-metal cations include onium cations, such as those based on sulfonium, oxonium, or iodonium. Preferably, the onium cations contain aryl or fluorinated aryl chromophores for enhanced sensitivity to actinic radiation.

Preferably, the cation $G^+$ is an onium cation having formula (II):

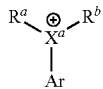

wherein $X^a$ is I or S, each $R^a$ and $R^b$ is independently a substituted or unsubstituted and is $C_{1-20}$ alkyl, $C_{1-20}$ fluoroalkyl, $C_{3-20}$ cycloalkyl, $C_{3-20}$ fluorocycloalkyl, $C_{2-20}$ alkenyl, $C_{2-20}$ fluoroalkenyl, $C_{6-20}$ aryl, $C_{6-20}$ fluoroaryl, $C_{7-20}$ aralkyl, or $C_{7-20}$ fluoroaralkyl, wherein where $X^a$ is S, $R^a$ and $R^b$ are separate or connected to each other by a single bond, and where $X^a$ is I, one of $R^a$ or $R^b$ is a lone pair of electrons, and Ar is a $C_{5-30}$ aromatic-containing group. Preferably, $R^a$ and $R^b$ are independently $C_{3-20}$ cycloalkyl or $C_{6-20}$ aryl.

Preferred cations $G^+$ have formula (III) or (IV):

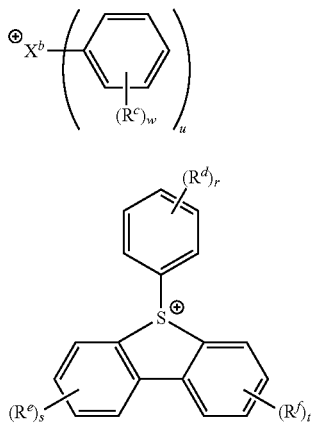

wherein $X^b$ is I or S; $R^c$, $R^d$, $R^e$, and $R^f$, are each independently hydroxy, nitrile, halogen, $C_{1-10}$ alkyl, $C_{1-10}$ fluoroalkyl, $C_{1-10}$ alkoxy, $C_{1-10}$ fluoroalkoxy, $C_{6-20}$ aryl, $C_{6-20}$ fluoroaryl, $C_{6-20}$ aryloxy, or $C_{6-20}$ fluoroaryloxy; u is an integer of 2 or 3, wherein when X is I, u is 2, and where X is S, u is 3, w and r are each independently an integer from 0 to 5, and s and t are each independently an integer from 0 to 4.

Preferred compounds for use as RAFT agents have formula (I-a):

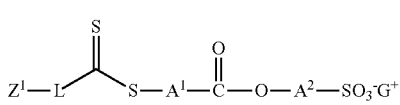

wherein L, $A^1$, $A^2$ and G are as defined in formula (I), and $Z^1$ is a substituted or unsubstituted $C_{1-20}$ alkyl, $C_{3-20}$ cycloalkyl, $C_{6-20}$ aryl, or $C_{7-20}$ aralkyl.

Also preferably, the RAFT compound has formula (I-b) or (I-c):

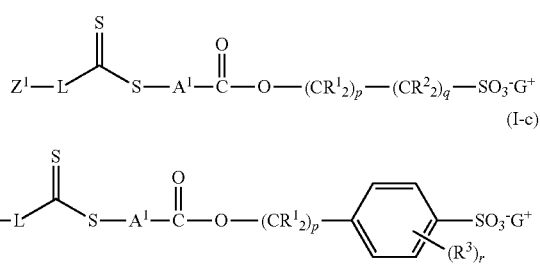

wherein L, $A^1$, and G are as defined in formula (I-a), $Z^1$ is a substituted or unsubstituted $C_{1-10}$ alkyl, $C_{3-10}$ cycloalkyl, $C_{6-10}$ aryl, or $C_{7-10}$ aralkyl, and $R^1$, $R^2$ and $R^3$ are independently H, F, $C_{1-10}$ alkyl, $C_{1-10}$ fluoroalkyl, $C_{3-10}$ cycloalkyl, or $C_{3-10}$ fluorocycloalkyl, p is an integer of from 0 to 10, q is an integer of from 1 to 10, and r is an integer of 0 to 4. Preferably, at least one of $R^2$ and $R^3$ contains fluorine.

Useful RAFT compounds include those having formula (I-b-1):

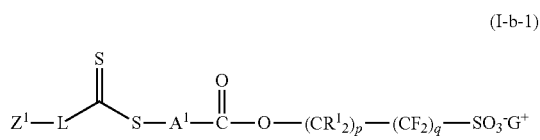

wherein $Z^1$, L, $A^1$, and G are as defined in Formula (I-b), and $R^1$ is H, F, $C_{1-10}$ alkyl, or $C_{1-10}$ fluoroalkyl, p is an integer of from 1 to 10, and q is an integer of from 1 to 10.

Alternatively, the RAFT compound includes those having formula (I-d):

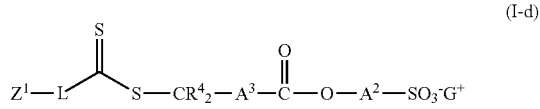

wherein $Z^1$, L, $A^2$ and G are as defined in Formula (I), each $R^4$ is independently H, CN, $C_{1-10}$ alkyl, $C_{6-10}$ aryl, or —C(=O)—$OR^5$ where $R^5$ is a $C_{1-10}$ alkyl or $C_{3-10}$ cycloalkyl, provided at least one $R^4$ is not H, and $A^3$ is ester-containing or non-ester containing and is $C_{1-10}$ alkylene, $C_{3-10}$ cycloalkylene, $C_{6-10}$ arylene, or $C_{7-10}$ aralkylene. Preferably, one $R^4$ is CN, $C_6$ aryl, or —C(=O)—$OR^5$ where $R^5$ is a $C_{1-3}$ alkyl and the remaining $R^4$ is H or $C_{1-3}$ alkyl, and $A^3$ is $C_{1-10}$ alkylene, $C_{3-10}$ cycloalkylene, $C_{6-10}$ arylene, or $C_{7-10}$ aralkylene.

Exemplary RAFT compounds include those chosen from formulas (I-d-1) to (I-d-6):

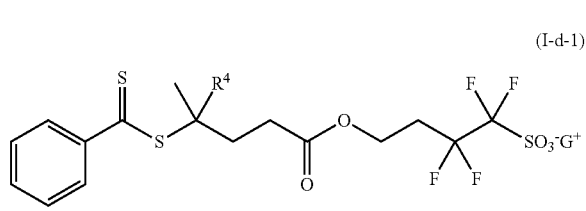

-continued

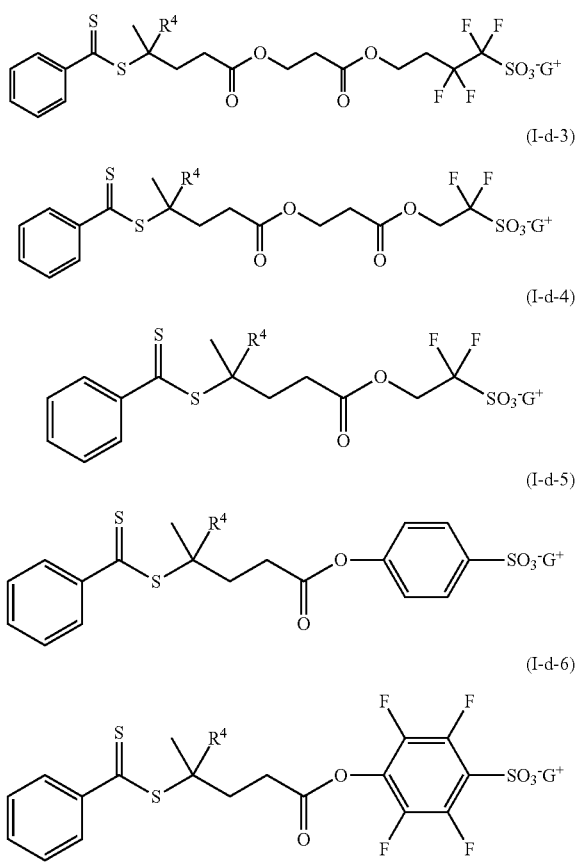

wherein G+ is as defined for formula (I) and R⁴ is CN, C₆ aryl, or —C(=O)—OR⁵ where R⁵ is a C₁₋₃ alkyl.

Further, a polymer can be prepared, which includes end groups derived from the reaction product of the RAFT compound, an unsaturated monomer, and optionally, an initiator.

As defined herein, "unsaturated monomer" includes those monomers having a polymerizable double or triple bond, such as, for example, olefins including ethylene, propylene, tetrafluoroethylene, etc., acetylene, propyne, cyclic olefins such as those based on norbornenes, aromatic unsaturated compounds such as styrenes and stilbenes, alpha-beta unsaturated compounds such as (meth)acrylates including their parent acids, crotonates, maleic and fumaric acid derivatives such as maleic anhydride, and the like. Preferred unsaturated monomers compatible with RAFT polymerization processes include styrenes and (meth)acrylates. It should be noted that as used herein, the term "(meth)acrylates" includes both acrylates and methacrylates.

A method of making the polymer includes polymerizing one or more unsaturated monomers in the presence of a compound of the formula (I); and optionally, an initiator. Any monomer copolymerizable under RAFT conditions may be useful in preparing the monomer. Preferably, the polymer comprises monomers including: an acid-deprotectable monomer having acid labile protecting groups such as tertiary cyclic or acyclic alkyl esters, ketals, acetals, and benzylic esters, masking a base-soluble functional group such as a phenolic group or carboxylic acid group; a base-soluble monomer having base-soluble functional groups such as a phenolic group, carboxylic acid group, or hexafluoroisopropanol group; a lactone-containing monomer; and optionally, a photoacid-generating monomer.

Suitable initiators may include any radical initiator useful in the art, such as peroxy initiators, diazo initiators, and the like. For example, peroxy initiators such as tert-butyl hydroperoxide, tert-butyl peroxy 2-ethyl hexanoate (tert-butyl peroctoate), t-butyl peroxy pivalate, tert-butyl peroxy benzoate, di-benzoyl peroxide, tert-butyl peroxy isobutyrate, diazo initiators such as azobis isobutyronitrile (AIBN), 4,4-azobis(4-cyanovaleric acid); and the like. Preferred initiators include those sold under the tradename VAZO by DuPont, such as VAZO 52, VAZO 67, VAZO 88, and V-601 initiator from Wako. Alternatively, the polymerization may be carried out by thermal initiation (e.g., greater than about 120° C., more preferably greater than about 150° C.). Preferably, thermal initiation may be used where one or more component monomers are styrenic.

The polymer may thus be prepared by radically or thermally initiated polymerization of the monomers in a degassed solvent, in the presence of the chain transfer agent, using the aforementioned reversible addition-fragmentation transfer (RAFT) process. The polymerization may be carried out in batch mode, by batch addition of monomers and/or initiator to the reaction mixture containing the chain transfer addition, by metered addition of separate feeds of one or more of the monomers and/or initiator and/or chain transfer agent to the reaction mixture, or any other suitable method for combining the reactants. It will be appreciated that block copolymers may be produced by sequential addition of monomers for each block to the reaction mixture, or a polymer having a graded composition may be formed by gradually changing the monomer proportions and/or composition in the feed over time. All such polymers preparable by the RAFT method are contemplated herein.

The polymer may have a weight averaged molecular weight (Mw) of 1,000 to 100,000 g/mol, preferably 1,500 to 50,000 g/mol, more preferably 2,000 to 25,000 g/mol, and still more preferably 3,000 to 15,000 g/mol. The polymer may also have a number averaged molecular weight (Mn) of 500 to 100,000 g/mol, preferably 1,000 to 50,000 g/mol, more preferably 1,500 to 25,000 g/mol, and still more preferably 2,000 to 15,000 g/mol. Molecular weights may be determined using any suitable method, such as gel permeation chromatography (GPC) using a crosslinked styrene-divinylbenzene column calibrated to polystyrene standards by universal calibration, at a flow rate of about 1 ml/min. The polymer polydispersity (Mw/Mn) is preferably less than 2.0, more preferably less than or equal to 1.8, more preferably less than or equal to 1.6, and more preferably less than or equal to 1.5.

The invention is further illustrated by the following examples. All compounds and reagents used below are available commercially except where a procedure is provided. Triphenylsulfonium 1,1-difluoro-2-(methacryloyloxy)ethane-1-sulfonate (the TPS F2 PAG monomer) was obtained commercially from Central Glass.

Structural characterization was carried out by nuclear magnetic resonance (NMR) spectrometry on an INOVA 500 NMR Spectrometer (operating at 500 MHz for ¹H and 125 MHz for ¹³C) or INOVA 400-MR NMR Spectrometer (operating at 400 MHz for ¹H and 376 MHz for ¹⁹F), each from Varian. Polymer composition was determined by quantitative ¹³C NMR at 125 MHz using NOE suppression techniques (i.e., Cr(acetylacetonate)₃ and a pulse delay of 2 seconds). Molecular weight (Mw) and polydispersity (PD) were determined by gel permeation chromatography (GPC) using a sample concentration of 1 mg/ml and a crosslinked styrene-divinylbenzene column with universal calibration curve calibrated with polystyrene standards, and eluted with tetrahydrofuran containing 0.2 wt % lithium nitrate at a flow rate of 1 ml/min.

Synthesis of PAG-Functionalized Chain Transfer Agent CTA1 was carried out according to the following procedure, and as illustrated in Scheme 1 (note that as used herein, "TPS" denotes "triphenylsulfonium").

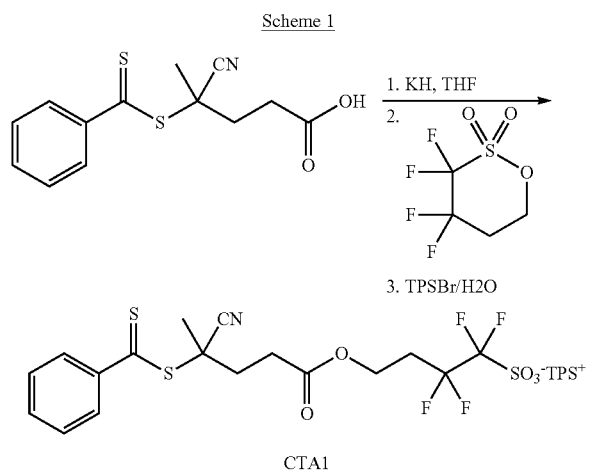

4-cyano-4-(thiobenzoylthio)pentanoic acid (0.550 g, 1.97 mmol) was transferred under inert atmosphere to a 20 mL vial and dissolved in 2 g anhydrous THF. To the resulting red solution, KH (0.158 g, 3.94 mmol) was added in small portions over 5 minutes). After the addition, bubbling had stopped and excess KH remained in the darker red colored solution of the anion.

Distilled 3,3,4,4-tetrafluorobutanesultone (0.451 g, 2.17 mmol) was added to a 20 mL vial. Potassium acid solution was filtered through a frit into the vial containing the sultone, and the mixture stirred at room temperature for 2 h., at which point the solution was removed from the glove box and crude product washed with hexanes (approximately 10 g). A bottom phase of crude product separated as a red oil. The upper light pink hexanes solution was discarded and the red oily crude product redissolved in THF and extracted a second time with hexanes. The resulting twice-extracted oil was used in the next step without further purification.

In the subsequent (metathesis) step, the red oil was dissolved in $CH_2Cl_2$ (5 mL) and an aqueous solution of triphenylsulfonium bromide (0.743 g, 2.166 mmol, dissolved in 5 mL of deionized water) was added. The biphasic mixture was shaken vigorously to intermix the phases, and the mixture stirred overnight at room temperature. The aqueous layer was initially pink in color, but over time became colorless. After 18 h., the aqueous layer was removed and the organic phase washed two times with DI water. The organic phase was then dried over $MgSO_4$ and the solvent removed by rotary evaporation to afford a viscous red oil (1.27 g, 86% yield). The product was analyzed by $^1H$ and $^{19}F$ NMR spectroscopy. $^1H$ NMR (400 MHz, $CDCl_3$): δ 7.91 (d, $^3J$=8.5 Hz, 2H), 7.66-7.78 (m, 15H), 7.55 (t, $^3J$=7.5 Hz, 1H), 7.37 (t, $^3J$=7.4 Hz, 2H), 4.4 (t, $^3J$=6.6 Hz, 2H), 2.40-2.85 (m, 6H), 1.9 (s, 3H). $^{19}F$ NMR ($CDCl_3$): −112.3 (m, 2F), −118.3 (m, 2F).

A polymer (Polymer Example 1) was prepared using PAG endgroup compound CTA1 according to the following method and as shown in Scheme 2.

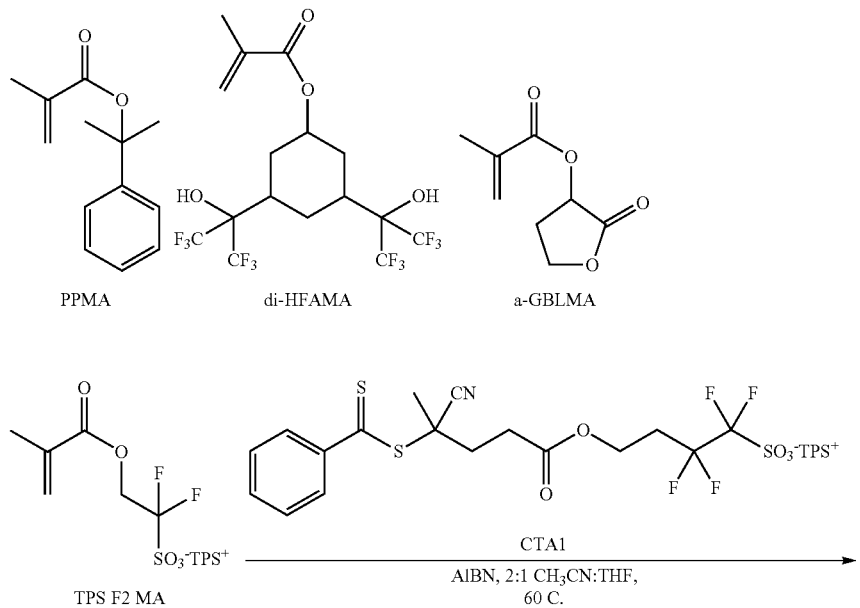

2-phenyl-2-propyl methacrylate (PPMA; 1.50 g, 7.34 mmol), alpha-(gamma-butyrolactone)methacrylate (a-GBLMA, 1.82 g, 10.7 mmol), 3,5-bis(1,1,1,3,3,3-hexafluoro-2-hydroxypropan-2-yl)cyclohexyl methacrylate (di-HFAMA, 1.41 g, 2.83 mmol), and triphenylsulfonium 1,1-difluoro-2-(methacryloyloxy)ethane-1-sulfonate (TPS-F2 MA, 0.832 g, 1.69 mmol) were transferred under inert atmosphere into a 20 mL vial to provide a monomer mixture. 8.3 g of a solvent mixture was prepared by combining $CH_3CN$:anhydrous tetrahydrofuran (THF) in a 2:1 (v/v) ratio. About half of the solvent mixture was added to the monomers to dissolve them fully and the resulting monomer solution filtered through a plug of oven-dried neutral alumina directly into a fresh vial, followed by a wash of the plug with the remaining solvent.

A solution of CTA1 (0.991 g, 0.661 mmol, 50 wt % solution in anhydrous THF) was then added to the vial, and dissolved to provide a red, homogeneous solution. 2,2'-azobis (2-methylpropionitrile) (AIBN; 0.660 mL, 0.132 mmol, 0.2 M in toluene) was added and the vial was capped and heated to 60° C. for 72 h. The solution was cooled to room temperature and precipitated into 100 mL 90:10 (v/v) methyl tert-butyl ether/isopropanol (MTBE:iPrOH) twice, where the precipitated polymer was collected by filtration and redissolved in 6 mL THF between precipitations. After the second precipitation, the solid polymer was collected by vacuum filtration and dried in a vacuum oven at 45° C. overnight to yield the polymer as a pink solid. $^{13}$C NMR (100 MHz, acetone-$d_6$) composition 25:42:12:21 mole % ratio of PPMA/a-GBLMA/di-HFAMA/TPS-F2 PAG, respectively; Mn=6600 g/mol, Mw=7600 g/mol, PDI=1.15.

A second polymer (Polymer Example 2) was prepared without a PAG monomer but with CTA1, according to the following procedure and according to Scheme 3.

methylpropionitrile) (AIBN; 0.603 mL, 0.121 mmol, 0.2 M in toluene) was added and the vial was capped and heated to 60° C. for 72 h. The solution was cooled to room temperature and precipitated into 100 mL 90:10 (v/v) methyl tert-butyl ether/isopropanol (MTBE:iPrOH) twice, where the precipitated polymer was collected by filtration and redissolved in 6 mL THF between precipitations. After the second precipitation, the solid polymer was collected by vacuum filtration and dried in a vacuum oven at 45° C. overnight to yield the polymer as a pink solid. $^{13}$C NMR (100 MHz, acetone-$d_6$) composition 25:42:12:21 mole-% ratio of PPMA/a-GBLMA/di-HFAMA, respectively, Mn=7200 g/mol, Mw=8600 g/mol, PDI=1.20.

A second PAG functionalized chain transfer agent (CTA2) having a phenyl dibenzothiophenium (PDBT) cation was prepared according to the following procedure, as illustrated in Scheme 2.

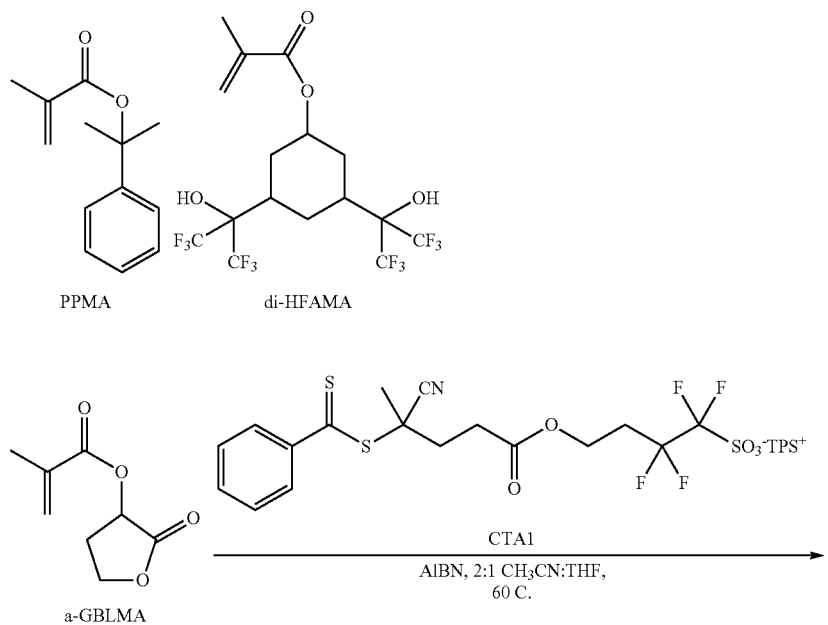

2-phenyl-2-propyl methacrylate (PPMA, 1.50 g, 7.34 mmol), alpha-(gamma-butyrolactone)methacrylate (a-GBLMA, 1.87 g, 11.0 mmol), and 3,5-bis(1,1,1,3,3,3-hexafluoro-2-hydroxypropan-2-yl)cyclohexyl methacrylate (di-HFAMA, 1.28 g, 2.56 mmol) were transferred under inert atmosphere to a 20 mL vial. 7.0 g of a solvent mixture was prepared by combining CH$_3$CN:THF in a 2:1 (v/v) ratio. About half the solvent mixture was added to the monomers to dissolve them fully and the monomer solution filtered through a plug of oven-dried neutral alumina directly into a fresh vial, followed by passing the remaining solvent through the alumina.

A solution of CTA1 (0.903 g, 0.602 mmol, 50 wt % solution in anhydrous THF) was transferred to the vial and a red, homogeneous solution formed. A solution of 2,2'-azobis(2-

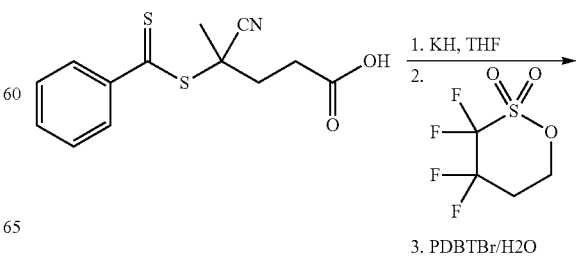

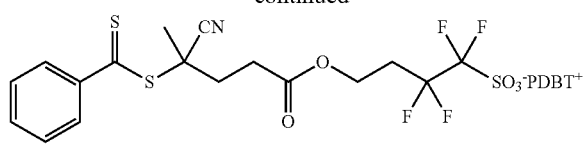

CTA2

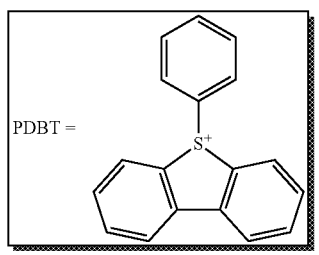

4-cyano-4-(thiobenzoylthio)pentanoic acid (1.00 g, 3.58 mmol) was transferred under inert atmosphere to a 20 mL vial and dissolved in 4 g anhydrous THF. To this red solution, KH (0.287 g, 7.16 mmol) was added in portions over 5 minutes. The red color of the solution darkened during addition of the KH.

Distilled 3,3,4,4-tetrafluorobutanesultone (0.820 g, 3.94 mmol) was added to a second 20 mL vial. The red solution containing the potassium salt of the RAFT agent was filtered through a frit into the vial containing the sultone, and this mixture was stirred at ambient temperature for 2 h. The crude was extracted with hexanes (approximately 10 g). The crude product separated as a red oil. The light pink hexanes solution was discarded and the red oily residue redissolved in THF and extracted a second time with hexanes.

The red oil was then dissolved in $CH_2Cl_2$ (10 mL) and an aqueous solution of phenyldibenzothiophenium bromide (PDBTBr; 1.34 g, 3.94 mmol, dissolved in 30 mL deionized water) was added and the combination shaken vigorously and the mixture stirred at ambient temperature for 12 hours. The aqueous layer was initially pink in color, but became colorless.

The aqueous layer was removed and the organic layer washed with DI water (2×30 mL), dried over $MgSO_4$, and the solvent removed by rotary evaporation to afford PAG functionalized chain transfer agent (CTA2) as a viscous red oil. Yield: 2.24 g (83.7%). The product was analyzed by $^1H$ and $^{19}F$ NMR spectroscopy. $^1H$ NMR (400 MHz, $CDCl_3$): δ 8.16 (dd, $^3J$=8.0 Hz, $^1J$=26 Hz, 4H), 7.80-7.90 (m, 4H), 7.47-7.68 (m, 8H), 7.35-7.40 (m, 2H), 4.41 (t, $^3J$=6.6 Hz, 2H), 2.36-2.87 (m, 6H), 1.91 (s, 3H). $^{19}F$ NMR ($CDCl_3$): −112.3 (m, 2F), −118.3 (m, 2F).

A third polymer (Polymer Example 3) containing a PAG-Functionalized CTA with PDBT Cation was prepared according to the following procedure, and as shown in Scheme 5.

Scheme 5

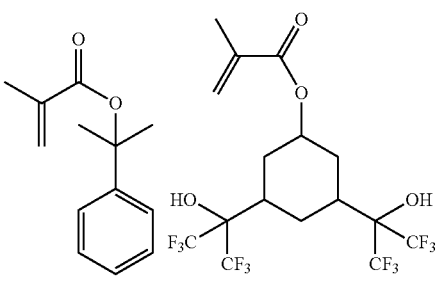

PPMA    di-HFAMA

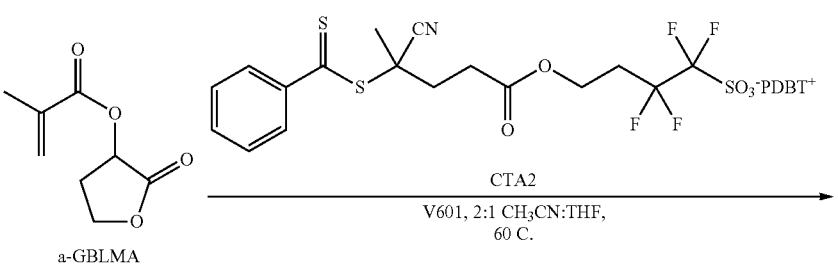

a-GBLMA

CTA2
V601, 2:1 $CH_3CN$:THF, 60 C.

All monomers (PPMA: 2.00 g, 9.79 mmol; di-HFAMA: 1.70 g, 3.41 mmol; a-GBLMA: 2.50 g, 14.7 mmol) were transferred to a 20 mL vial under inert atmosphere. A second 20 mL vial was charged with 9.3 g of a solvent mixture of 2:1 (v/v) CH$_3$CN:THF (sufficient to provide a 40% solids mixture). About half of this solvent mixture was added to the monomers to dissolve them, and the monomer solution filtered through a plug of oven-dried neutral alumina (~2 cm) directly into a fresh vial. The alumina plug was eluted with the remaining solvent mixture and the eluent collected in the vial. A solution of CTA2 (1.32 g, 0.881 mmol, 50 wt % solution in anhydrous THF) was transferred into the monomer-containing vial to produce a red, homogeneous solution. A solution of 2,2'-azobis(methyl 2-methylpropionate) (V601 initiator, available from Wako; 0.0406 mL, 0.176 mmol) was added to the monomer solution and the vial was capped and heated to 60° C. for 26 h. with stirring. Conversion was considered adequate based on crude $^1$H NMR spectroscopy of an aliquot, and the polymer was precipitated into 90 mL diisopropyl ether (i-Pr$_2$O), filtered, and dried overnight at 40° C. under vacuum to yield 5.9 g of polymer. The polymer was analyzed by GPC: Mn=6300 g/mol, Mw=7100 g/mol, PDI=1.12.

Polymer Example 3 was further treated under conditions to remove the dithioester RAFT end group as follows. The polymer (5.9 g, 0.931 mmol), V601 initiator (2.14 g, 9.31 mmol), and lauroyl peroxide (0.742 g, 1.86 mmol) were combined in a 100 mL round bottom flask under inert atmosphere. 15 g of anhydrous CH$_3$CN was added and heated while stirring to fully dissolve all solids. The flask was heated to reflux at 80° C. for 2.5 h. with vigorous stirring. After that time the color had changed to light orange and the flask was removed from the heat and cooled to RT. The sulfur-free polymer was precipitated into 150 mL i-Pr$_2$O, and an off-white solid was collected by filtration from the light pink solution. The collected polymer was washed with diethyl ether (2×10 mL) to afford a white solid. The solid was dried under N$_2$ and under vacuum at 40° C. to yield 4.5 g of polymer. GPC analysis: Mn=7100 g/mol, Mw=8300 g/mol, PDI=1.18. Relative monomer ratios from $^{13}$C NMR integrations: PPMA: 32%, a-GBLMA: 57%, di-HFA: 11%.

All ranges disclosed herein are inclusive of the endpoints, and the endpoints are independently combinable with each other. The suffix "(s)" as used herein is intended to include both the singular and the plural of the term that it modifies, thereby including at least one of that term. "Optional" or "optionally" means that the subsequently described event or circumstance can or cannot occur, and that the description includes instances where the event occurs and instances where it does not. As used herein, "combination" is inclusive of blends, mixtures, alloys, or reaction products. All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another.

The invention claimed is:

1. A compound having formula (I):

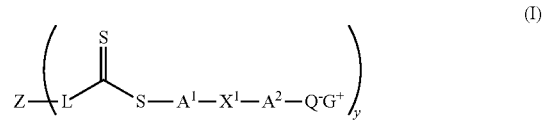

wherein in formula (I):
Z is a y valent C$_{1-20}$ organic group,
A$^1$ and A$^2$ are each independently ester containing or non-ester containing and are fluorinated or non-fluorinated, and are independently C$_{1-40}$ alkylene, C$_{3-40}$ cycloalkylene, C$_{6-40}$ arylene, or C$_{7-40}$ aralkylene, and A$^1$ contains a nitrile, ester, or aryl substituent group alpha to the point of attachment with sulfur,
L is a heteroatom or a single bond,
X$^1$ is a single bond, —O—, —S—, —C(=O)—O—, —O—C(=O)—, —O—C(=O)—O—, —C(=O)—NR—, —NR—C(=O)—, —NR—C(=O)—NR—, —S(=O)$_2$—O—, —O—S(=O)$_2$—O—, —NR—S(=O)$_2$—, or —S(=O)$_2$—NR—, wherein R is H, C$_{1-10}$ alkyl, C$_{3-10}$ cycloalkyl or C$_{6-10}$ aryl,
Q$^-$ is an anionic group,
G$^+$ is a metallic or non-metallic cation, and
y is an integer from 1 to 6.

2. The compound of claim 1, wherein
Z is a C$_{1-20}$ alkyl, C$_{3-20}$ cycloalkyl, C$_{6-20}$ aryl, or C$_{7-20}$ aralkyl,
y is an integer from 1 to 4,
A$^1$ is a C$_{1-20}$ alkylene, C$_{3-20}$ cycloalkylene, C$_{6-20}$ arylene, or C$_{7-20}$ aralkylene substituted alpha to the point of attachment with sulfur with a CN, C$_{6-10}$ aryl, or a C$_{2-10}$ ester-containing organic group,
A$^2$ is fluorinated or non-fluorinated, and is C$_{1-20}$ alkylene, C$_{3-20}$ cycloalkylene, C$_{6-20}$ arylene, or C$_{7-20}$ aralkylene,
Q$^-$ is sulfonate, sulfate, sulfonamide anion, or sulfonimide anion group, and
G is an alkali metal cation, ammonium cation, alkylammonium cation, alkyl-aromatic ammonium cation, sulfonium cation, iodonium cation, phosphonium cation, or a carbonium cation.

3. The compound of claim 1, the compound having formula (I-a):

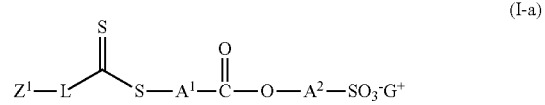

wherein L, A$^1$, A$^2$ and G are as defined in formula (I), and Z$^1$ is a substituted or unsubstituted C$_{1-20}$ alkyl, C$_{3-20}$ cycloalkyl, C$_{6-20}$ aryl, or C$_{7-20}$ aralkyl.

4. The compound of claim 3, the compound having formula (I-b) or (I-c):

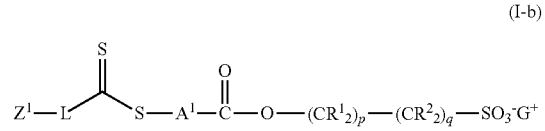

-continued (I-c)

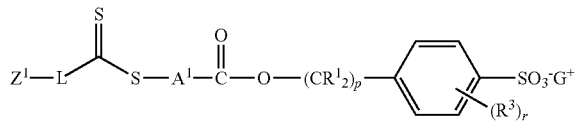

wherein L, A¹, and G are as defined in Formula (I-a), Z¹ is a substituted or unsubstituted $C_{1-10}$ alkyl, $C_{3-10}$ cycloalkyl, $C_{6-10}$ aryl, or $C_{7-10}$ aralkyl, and R¹, R² and R³ are independently H, F, $C_{1-10}$ alkyl, $C_{1-10}$ fluoroalkyl, $C_{3-10}$ cycloalkyl, or $C_{3-10}$ fluorocycloalkyl, p is an integer of from 0 to 10, q is an integer of from 1 to 10, and r is an integer of 0 to 4.

5. The compound of claim 4, having formula (I-b-1):

(I-b-1)

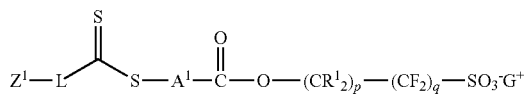

wherein Z¹, L, A¹, and G are as defined in formula (I-b), and R¹ is H, F, $C_{1-10}$ alkyl, or $C_{1-10}$ fluoroalkyl, p is an integer of from 1 to 10, and q is an integer of from 1 to 10.

6. The compound of claim 3, the compound having formula (I-d):

(I-d)

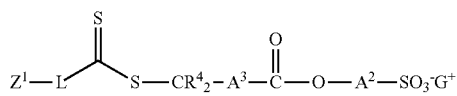

wherein Z¹, L, A² and G are as defined in Formula (I-a), each R⁴ is independently H, CN, $C_{6-10}$ aryl, or —C(=O)—OR⁵ where R⁵ is a $C_{1-10}$ alkyl or $C_{3-10}$ cycloalkyl, provided at least one R⁴ is not H, and A³ is ester-containing or non-ester containing and is $C_{1-10}$ alkylene, $C_{3-10}$ cycloalkylene, $C_{6-10}$ arylene, or $C_{7-10}$ aralkylene.

7. The compound of claim 1, wherein G⁺ is a cation of formula (II):

(II)

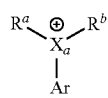

wherein Xᵃ is I or S, each Rᵃ and Rᵇ is independently substituted or unsubstituted and is a lone pair of electrons, $C_{1-20}$ alkyl, $C_{1-20}$ fluoroalkyl, $C_{3-20}$ cycloalkyl, $C_{3-20}$ fluorocycloalkyl, $C_{2-20}$ alkenyl, $C_{2-20}$ fluoroalkenyl, $C_{6-20}$ aryl, $C_{6-20}$ fluoroaryl, $C_{7-20}$ aralkyl, or $C_{7-20}$ fluoroaralkyl, wherein where Xᵃ is S, Rᵃ and Rᵇ are separate or connected to each other by a single bond, and where Xᵃ is I, one of Rᵃ or Rᵇ is a lone pair of electrons, and Ar is a $C_{5-30}$ aromatic-containing group.

8. The compound of claim 1 chosen from formulas (I-d-1) to (I-d-6):

(I-d-1)

(I-d-2)

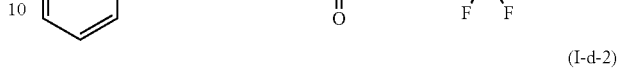

(I-d-3)

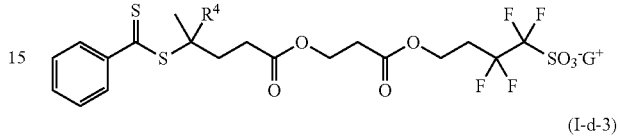

(I-d-4)

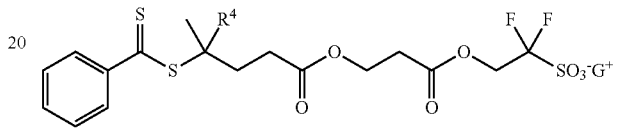

(I-d-5)

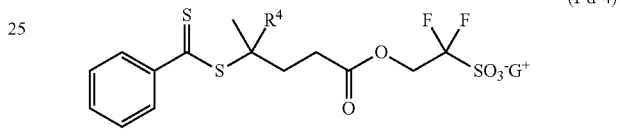

(I-d-6)

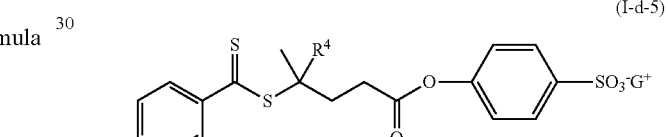

wherein G⁺ is as defined for formula (I) and R⁴ is CN, $C_6$ aryl, or —C(=O)—OR⁵ where R⁵ is a $C_{1-3}$ alkyl.

9. A polymer comprising end groups derived from the reaction product of the compound of claim 1, an unsaturated monomer, and optionally, an initiator.

10. A method of making a polymer, comprising:
polymerizing one or more unsaturated monomers in the presence of a compound having formula (I):

(I)

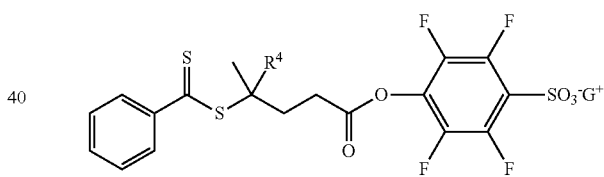

wherein in formula (I):
Z is a y valent $C_{1-20}$ organic group,
A¹ and A² are each independently ester containing or non-ester containing and are fluorinated or non-fluorinated, and are independently $C_{1-40}$ alkylene, $C_{3-40}$ cycloalkylene, $C_{6-40}$ arylene, or $C_{7-40}$ aralkylene, and $A^1$ contains a nitrile, ester, or aryl substituent group alpha to the point of attachment with sulfur, L is a heteroatom or a single bond, $X^1$ is a single bond, —O—, —S—, —C(=O)—O—, —O—C(=O)—, —O—C(=O)—O—, —C(=O)—NR—, —NR—C(=O)—, —NR—C(=O)—NR—, —S(=O)$_2$—O—, —O—S(=O)$_2$—O—, —NR—S(=O)$_2$—, or —S(=O)$_2$—NR—, wherein R is H, $C_{1-10}$ alkyl, $C_{3-10}$ cycloalkyl or $C_{6-10}$ aryl, $Q^-$ is an anionic group, $G^+$ is a metallic or non-metallic cation, and y is an integer from 1 to 6; and optionally, an initiator.

\* \* \* \* \*